(12) United States Patent
Hampe et al.

(10) Patent No.: US 10,292,785 B2
(45) Date of Patent: May 21, 2019

(54) GRIP FOR A MEDICAL DEVICE

(71) Applicant: Drägerwerk AG & Co. KGaA, Lübeck (DE)

(72) Inventors: Markus Hampe, Lübeck (DE); Gunnar Wiegandt, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 312 days.

(21) Appl. No.: 15/097,694

(22) Filed: Apr. 13, 2016

(65) Prior Publication Data

US 2016/0302879 A1 Oct. 20, 2016

(30) Foreign Application Priority Data

Apr. 17, 2015 (DE) .......................... 10 2015 004 952

(51) Int. Cl.
*A61B 90/30* (2016.01)
*A61B 90/00* (2016.01)
*A61B 90/35* (2016.01)

(52) U.S. Cl.
CPC .............. *A61B 90/36* (2016.02); *A61B 90/30* (2016.02); *A61B 90/35* (2016.02); *A61B 2560/04* (2013.01)

(58) Field of Classification Search
CPC ............................................... A61B 2090/308
See application file for complete search history.

(56) References Cited

U.S. PATENT DOCUMENTS

| 4,878,156 A | 10/1989 | Hallings et al. |
| 5,065,296 A | 11/1991 | Cude |
| 5,156,456 A | 10/1992 | Hoftman et al. |
| 5,493,757 A * | 2/1996 | Horan .................... A61B 90/36 16/422 |
| 2003/0014834 A1* | 1/2003 | Naughton ............... F21S 9/037 16/110.1 |
| 2014/0075721 A1 | 3/2014 | Denmark |
| 2014/0268751 A1 | 9/2014 | Boccoleri et al. |

FOREIGN PATENT DOCUMENTS

DE 10 2010 034 562 A1 2/2012

* cited by examiner

*Primary Examiner* — Nicholas W Woodall
(74) *Attorney, Agent, or Firm* — McGlew and Tuttle, P.C.

(57) ABSTRACT

A grip (1), for a medical device (2), has an inner part (3), which has fastening features (6) for fastening to the medical device (2) and an outer part (4), which has a snap-in element (5), which can lockingly engage an snap opposing element (7) of the inner part (3) for the detachable fastening of the outer part (4) to the inner part (3) and at least partially overlaps the inner part (3) on surfaces not facing the medical device. An actuating element (8) is provided on the outer part (4), and is manually actuatable for unlocking detachment. The actuating element (8) is configured in one piece with the snap-in element (5) and the outer part (4) such that the actuating element (8) performs a movement with the snap-in element (5) in relation to the snap opposing element (7) during the unlocking.

19 Claims, 6 Drawing Sheets

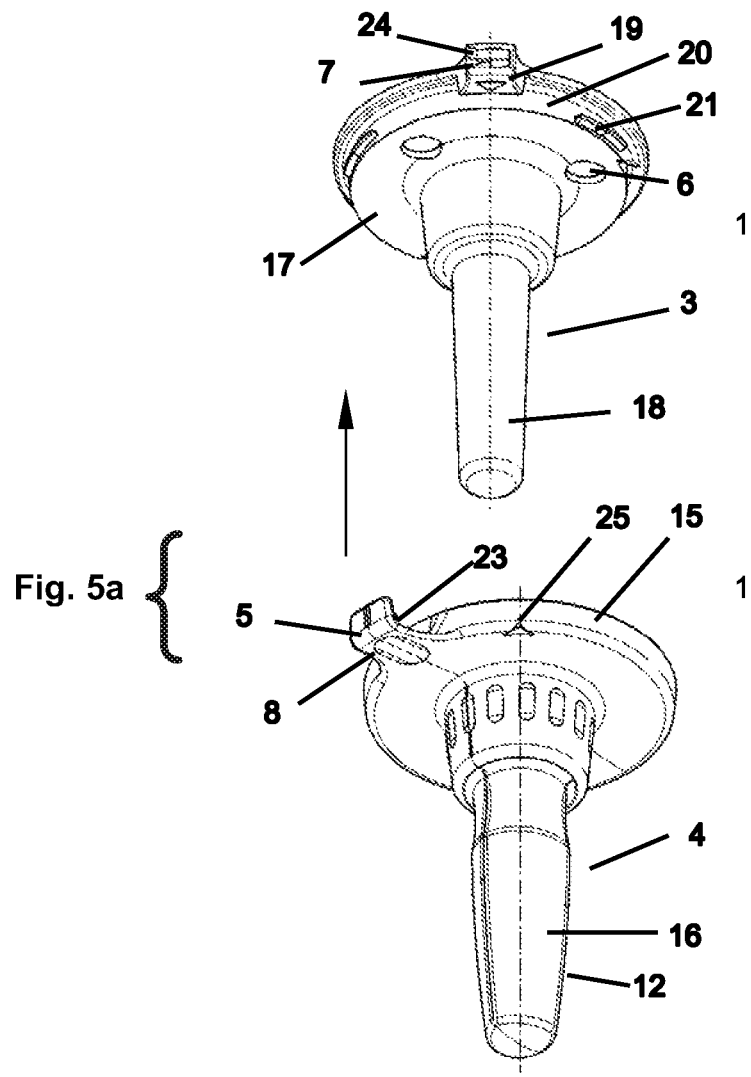

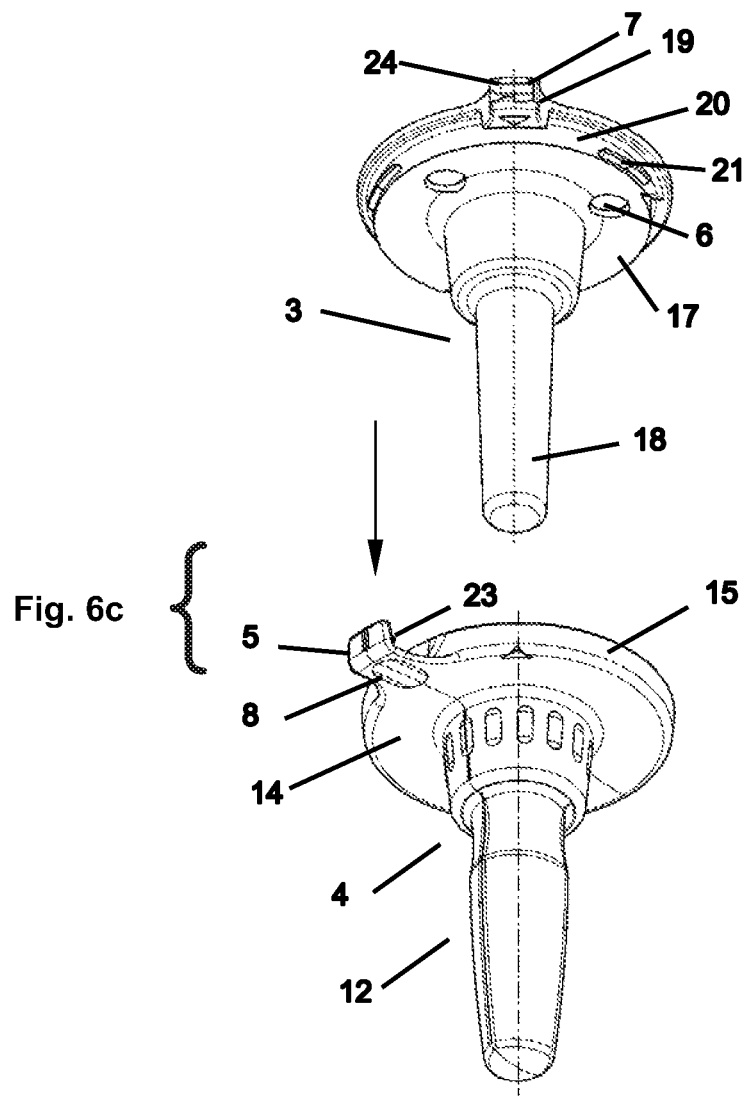

GRIP FOR A MEDICAL DEVICE

CROSS REFERENCE TO RELATED APPLICATIONS

This application claims the benefit of priority under 35 U.S.C. § 119 of German Patent Application 10 2015 004 952.6 filed Apr. 17, 2015, the entire contents of which are incorporated herein by reference.

FIELD OF THE INVENTION

The present invention pertains to a grip for a medical device with an inner part, which has means for fastening to the medical device, and with an outer part, which has a snap-in element, which can be meshed in a locking manner with an opposing element of the inner part for the detachable fastening of the outer part to the inner part. In the fastened state, the inner part is at least partially overlapped on its surfaces which are not facing the medical device, and further, an actuating element, by means of the manual actuation of which the locking is detachable, is provided on the outer part.

BACKGROUND OF THE INVENTION

A plurality of grips for medical devices, which shall make possible, particularly, a specific movement of the medical devices, are known from the state of the art. Besides the handling of corresponding grips, an essential feature of grips for medical devices is that these have to be easy to clean, disinfect and/or sterilize. In particular, grips, which are used in the operating area, and which are within the gripping range of the surgeon, have to be sterilized after completion of an operation. In order to make this possible, such grips are designed as being removable on a routine basis such that these can be removed and be sterilized in a sterilizer in a simple manner.

In this connection, there are medical devices such as, for example, operating lamps, which are at least partly located in the sterile operating area and which are grasped by the surgeon during an operation and are brought into the position needed in the particular case. After completion of an operation, it is necessary to sterilize the grips of the corresponding devices. In particular, in the case of operating lamps, the sterilization takes place by the corresponding grips being removed and being sterilized in a sterilizer. In order to make possible an as simple as possible removal of the grip, these grips often have a locking mechanism with an actuating element, via which a spring-loaded snap-in element can be actuated and thus the locking can be detached. An essential feature in the design of corresponding actuating elements as well as of triggering mechanisms connected to same is that these elements shall preferably be actuated with one hand such that it is possible in a simple manner for a user to remove a corresponding grip from the lamp.

In this connection, an operating lamp that has a grip assembly unit in the center of the housing lower part is well known from DE 10 2010 034 562 A1. The described grip assembly unit essentially has a fixed, especially rotationally fixed, handle with a size which is suitable for being grasped comfortably by the attending physician with one hand or at least with the fingers so that the operating lamp can be swiveled in conjunction with the swivel arm system into the desired position as needed. For the use of the grip assembly unit in the sterile area, it is essential that at least the handle must be sterile. In order to achieve this, a special design of the grip assembly unit described provides that the gripping element of the handle be designed as a replaceable part, which can be removed from the operating lamp after actuating the actuating element of a locking mechanism and sterilized in a simple manner.

All prior-art grips for medical devices, in particular for examination lamps or operating lamps, have the drawback that either gaps are present in the area of the actuating mechanism that are difficult to clean, disinfect or sterilize, or else that parts of the actuating mechanism, in particular corresponding, spring-loaded knobs, are provided in the sterile area of a grip assembly unit and would have to be sterilized partially separately. Further undesired properties of grips, designed as removable, on medical devices are an inadmissibly high backlash, unfavorable mounting conditions, in particular provided that a mounting is only possible in defined angular positions, as well as the providing of a gripping surface with a nonergonomic design.

SUMMARY OF THE INVENTION

Based on the solutions known from the state of the art as well as the problems explained above, a basic object of the present invention is to perfect a grip for a medical device such that the removal of the component to be sterilized from the grip assembly unit is possible in a simple manner and without a great exertion of force, first and foremost in order to achieve a comparatively simple sterilization of the gripping surface. The fastening of a corresponding component to be sterilized shall also be possible in a simple manner and preferably only using one hand. Likewise, an ergonomic design and configuration of the gripping surface shall be provided and further it shall be ensured that the grip can also be cleaned, particularly disinfected easily and in a lasting manner in the mounted state on the medical device.

According to the present invention, a grip for a medical device—a medical device grip—comprises an inner part, which has a fastening means for fastening to the medical device, and an outer part, which has a snap-in element, which can be meshed in a locking manner with an opposing element (snap opposing element) of the inner part for the detachable fastening of the outer part to the inner part and which, in the fastened locked state, overlaps the inner part at least partially on the surfaces of the inner part which are not facing the medical device. An actuating element is provided on the outer part, by means of the manual actuation of which the locking is detachable. The actuating element is configured as one piece with the snap-in element and with the outer part such that the actuating element performs a movement with the snap-in element in relation to the snap opposing element during the unlocking. Thus, it is essential to the technical solution according to the present invention that a grip assembly unit, comprised of an outer part and an inner part, be provided, in which the outer part is made in one piece such that especially a contiguous, closed outer surface is provided, which has no gaps or the like. Such an outer part can preferably be manufactured as a plastic component, in particular by way of injection molding. In this connection, the molding is selected such that an ergonomically shaped gripping surface is provided, on the one hand, and, on the other hand, the outer surface has as few scores and other complicated geometries as possible such that these can be reliably cleaned in a simple manner.

In particular, a one-piece sterilizable outer part is provided by means of a grip configured according to the present invention. Furthermore, both the inner part and the outer part have an ergonomic design such that both the fastening and the detaching of the outer part are possible in a simple manner and, on the other hand, the operation of the handle, including the movement of the medical device, can be carried out without a great exertion of force. Since the inner part is almost entirely overlapped by the outer part and advantageously only a small gap remains between the medical device and the outer part, it is ensured that the likelihood of a contact of the grip with unsterile areas during an operation and during the locking and unlocking of the outer part is low. The mounting of the outer part onto the inner part regardless of the angular position or at least impervious to incorrect angular positions is advantageously possible. In this connection, the outer part may be designed and configured as a reusable component to be sterilized or as a disposable component, which is disposed of after its use. If the outer part is configured as a disposable component, it is particularly advantageous if this part has only a minimal wall thickness as can preferably be achieved in the manufacture as a blow molded component. In this connection, furthermore a thin-walled outer part, which is designed and configured as a disposable component, may be fastened to the inner part either directly or via a suitable adapter element.

In a special embodiment of the present invention, provisions are made for the inner part and/or the outer part to have a plastic at least on their outer surfaces. Both the inner part and the outer part are especially preferably made of a suitable plastic material. A polyamide, particularly PA12-GB30, is preferably used for the inner part, and a polyetherimide (PEI) is preferably used for the outer part according to special variants of the present invention. In any case, the material selection should be made such that the surfaces can be cleaned easily and, in particular, the outer part can be repeatedly sterilized without there being permanent damage to this component.

The locking according to the present invention is configured such that in the locked state, a force can be transmitted from the outer part via the inner part via the snap-in element and the snap opposing element. The snap-in element and the snap opposing element preferably have a wedge-shaped design and each have tapered sliding surfaces that are in contact with each other and are moved in relation to each other during the locking process. In the locked state, the snap-in element and the opposing element have each stop surfaces, which are in contact with each other in the locked state and thus make possible a low-backlash locking of the outer part with the inner part, on the one hand, and prevent an undesired detachment of the locking, on the other hand. The snap-in element of the outer part as well as the opposing element of the inner part are preferably configured such that without actuation of the actuating mechanism for unlocking, a detaching force is needed for unlocking, which far exceeds the force to be manually applied to the grip.

According to a special embodiment, the inner part has on its outer surface at least one thread, which can be meshed with a complementary thread arranged on an inside of the outer part. These two threads are preferably configured in the form of a right-hand thread. In the sense of this embodiment, a thread is also defined as an individual flank of a thread, which can be meshed with a correspondingly configured, complementary thread flank on a surface. According to a preferred embodiment, a threaded tooth is provided both on the inner part as well as on the outer part, which can be meshed with one another such that a movement of the outer part in relation to the inner part can be brought about by means of a rotary motion so that the outer part can consequently be brought into a locked position opposite the inner part.

Generally different geometries are suitable for the embodiment of the threaded tooth. The threaded tooth and/or thread preferably have a trapezoidal, sawtooth-shaped or pointed-tooth-shaped profile.

A screwing movement is preferably performed about and along a fixed axis during the locking of the outer part in relation to the inner part. In this case, a longitudinal displacement of the outer part toward the inner part occurs at the same time. In principle, a V thread, a trapezoidal thread, a round thread and a buttress thread may be employed as types of threads. In case of using threaded teeth, whose profile is trapezoidal or sawtooth-shaped, a comparatively low friction occurs between the outer part and the inner part during the rotary motion and the locking process connected thereto.

According to a special embodiment of the present invention the snap-in element may be arranged on a spring arm. In this case, the spring arm is configured in one piece with the outer part and preferably performs a relative movement toward the inner part during the locking process. In the locked state, the spring arm is in a slightly pretensioned state. However, the spring arm is loaded both for unlocking and locking such that it performs a movement to be able to carry out the corresponding process successfully. The spring arm preferably has the actuating element, which advantageously has a suitable gripping surface. Such a gripping surface is preferably changed in its surface properties compared to the surrounding surface and/or has a finger recess or thumb recess. In a special embodiment, the surface is polished in the area of the gripping surface, while the remaining surface of the outer part is matted. Of course, an exactly reverse design of the surfaces may also be provided.

Thus a user, in an especially ergonomic manner, may operate the actuating element provided on the spring arm for locking or unlocking the locking mechanism in order to thus detach the outer part from the inner part or to fasten it to same in a simple and rapid manner. According to a particularly suitable embodiment, an actuation of the actuating element is only necessary for detaching the outer part from the inner part while the snapping in automatically takes place during the locking. It is also ensured that a one-hand operation of the actuating element as well as a removal of the outer part from the inner part is possible.

A preferred embodiment of the outer part further provides that the outer part overlap the inner part in the fastened state on all surfaces not facing the medical device. The outer surface of the outer part can thus be used in the sterile area, for example, of an operating room and can be disinfected and/or sterilized in a simple manner after completion of an operation.

The inner part preferably has fastening means comprising passage holes, which are suitable for receiving screws or rivets, for fastening the grip to the medical device. By means of such a fastening means, the inner part is rigidly connected to the medical device and remains permanently on same. Only the outer part, which is fastened to the inner part by means of a suitable locking mechanism, can be removed, as needed, from the inner part and thus also from the medical device.

In addition to a grip for a medical device, the present invention also pertains, furthermore, to the use of a grip configured according to the present invention for an examination lamp and/or for an operating lamp. In this case, the grip is preferably arranged under the lamp in the light area, namely centrally. It is thus possible in a simple manner for the user to transfer the lamp into a position needed by the user by means of the grip. Consequently, it is, in principle, of no importance whether the lamp is standing on a floor, fastened to a device or to a ceiling support arm. The grip is rigidly connected via the inner part to the examination lamp or operating lamp such that the operator is optionally also able to move the lamp with the furthermore provided arms of a suspension. Of special importance for this is the fact that the snap-in element is configured such that an undesired detachment of the locking in the locked state is reliably avoided, on the one hand, and, on the other hand, the fact that the backlash between the snap-in element and the opposing element is limited to a minimum. In particular, the grip is connected to the inner part by the interaction of the snap-in element and additional fastening means, such as the above-described thread such that forces and torques can be readily transmitted in all directions in space.

The present invention is explained in detail below without limiting the general idea of the invention on the basis of exemplary embodiments and with reference to the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 5a is a perspective view showing the mounting of the outer part to the inner part of a grip;

FIG. 6c is a perspective view showing the removal of the outer part from the inner part of a grip.

DESCRIPTION OF THE PREFERRED EMBODIMENTS

Figure 1:
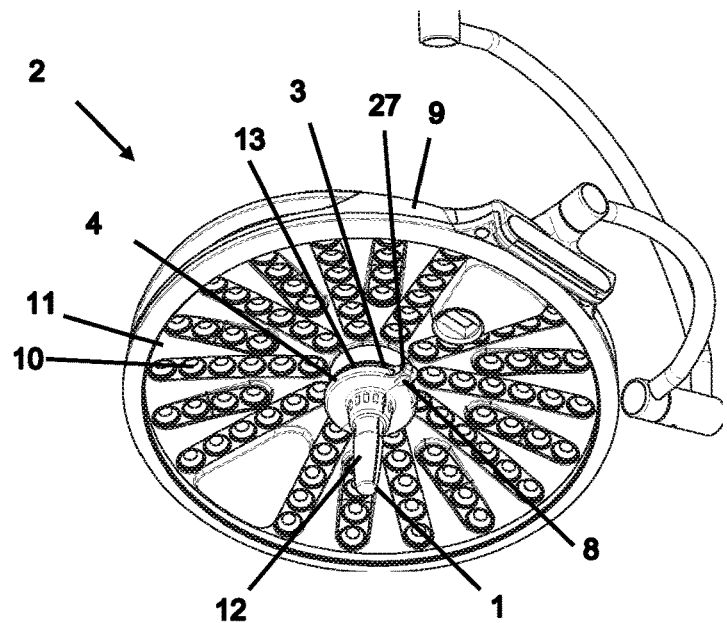
FIG. 1 is a perspective view of an operating lamp with a centrally arranged grip.

Referring to the drawings, FIG. 1 shows a medical device 2 in the form of an operating lamp, as it is usually fastened movably to a swiveling ceiling arm system. In this case, the operating lamp 2 has a light source 10, which is arranged in the light fixture housing 9 and which is configured such that the light beams emitted over a light emission area 11 are directed toward the work area. A grip 1, which is configured according to the present invention and which enables an operator, especially a physician, to bring the operating lamp 2 and possibly a ceiling arm system connected thereto into the position desired by the operator, is provided centrally in the middle of the light emission area 11. For adjustment, it is, in principle, of importance that this adjustment can be carried out without great exertion of force, on the one hand, and the lamp 2 remains in the position set by the operator, on the other hand.

The operating lamp 2 that is shown in FIG. 1 is used in the sterile area of an operating room and is operated, as needed, by a person involved in the operation. The gripping surface 12 of the grip 1 is thus in the sterile area and has to be at least disinfected after an operation and has to be sterilized after completion of a defined operation cycle, especially at the end of the day of an operation. For this, the grip 1 is configured such that a locking is released by actuating an actuating element 8 so that the outer part 4 of the grip 1 can be detached and thus removed from an inner part 3 fastened to the operating lamp 2 itself. Furthermore, individual parts of the grip 1 configured according to the present invention, which has essentially an inner part 3 fastened to the operating lamp 2 as well as a removable outer part 4, shall be explained in detail.

Figure 2:
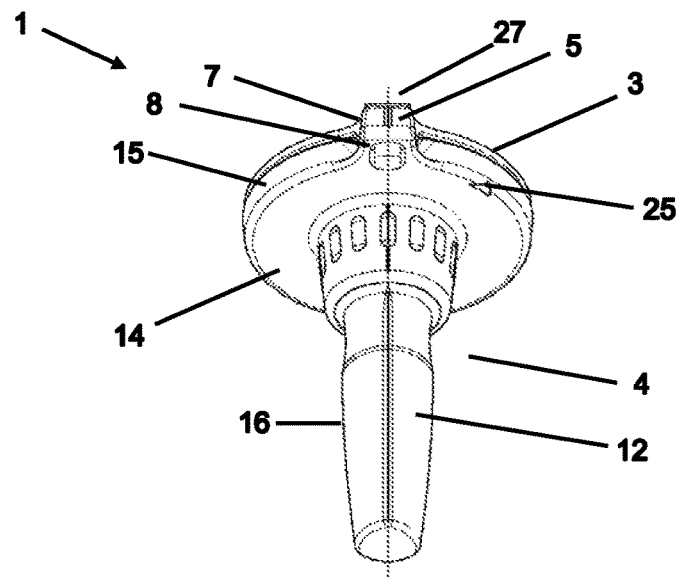
FIG. 2 is a perspective assembly view of the grip with an outer part as well as an inner part.

FIG. 2 shows a grip 1 for a medical device 2 in a perspective view, in which the grip 1 is preferably suitable for use for an operating lamp. The grip 1 has an inner part 3, which is connected to an outer part 4 via a locking mechanism 27, and the inner part and the outer part 3, 4 are made of a plastic material. The outer part 4 has a one-piece design such that it at least almost entirely overlaps the inner part 3 and only a small gap 13 remains between the outer part 4 and the inner part 3 in the mounted and locked state.

The outer part 4 has a plate-like basic element 14 with a contact protection collar 15, which encloses the inner part 3. A shaft 16, which is at least approximately cylindrical, with a gripping surface 12, is connected to the basic element 14. The shaft 16 with the gripping surface 12 is shaped ergonomically such that a comfortable grasping and a good hold in the hand of the operator are ensured.

An actuating element 8 in the form of a spring arm, that has a snap-in element 5, is provided on the basic element 14 in the area of the contact protection collar 15. By pressing the actuating element 8, the snap-in element 5 is moved in the direction of the inner part 3 and at first the locking between the outer part 4 and the inner part 3 is released. The outer part 4 can subsequently be entirely removed from the inner part 3 by means of a counterclockwise rotary motion. The detachment and removal of the outer part 4 with one hand is preferably possible by the actuating element 8 being operated by the thumb.

As soon as the outer part 4 is locked by means of the snap-in element 5, which element meshes (engages) with a complementary opposing element (snap opposing element) 7 in the inner part 3, the rotary motion of the outer part 4 relative to the inner part 3 is blocked in both directions of rotation. The outer part 4 is locked in a low-backlash manner in relation to the inner part 3 such that a simple and precise operation of the medical device 2 connected to the grip 1 is made possible. The one-piece design of the outer part 4 with the snap-in element 5 provided thereon, which has a suitable snap-in contour 23, and the actuating or operating element 8, is essential. A closed surface, which is simple and reliable to clean, to disinfect and/or to sterilize, is provided by the closed surface of the outer part 4 with its contact protection collar 15. In this case, it is possible in a comparatively simple manner by means of the locking mechanism 27 to remove the outer part 4 from the inner part 3 and to make it available for a sterilization process. The outer part 4 can be detached by the spring arm actuating element 8, with the snap-in element 5, on which is provided a thumb recess or finger recess, being pressed such that the locking mechanism 27 is released.

Figures 3A, 3B:
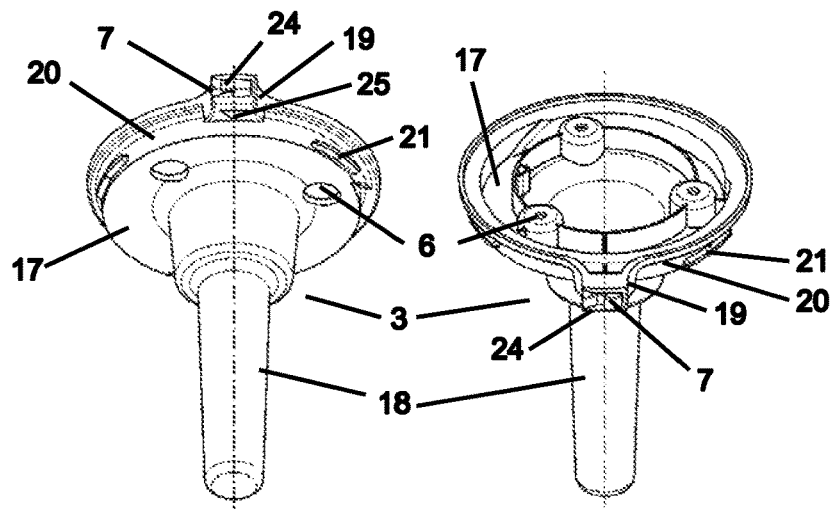
FIG. 3a is a lower perspective view of the inner part of the grip.
FIG. 3b is an upper perspective view of the inner part of the grip.

FIGS. 3a and 3b show in two perspective views the inner part 3 of a grip 1 configured according to the present invention for a medical device 2, with such a grip 1 being particularly suitable for being fastened to an operating lamp. In this connection, FIG. 3a shows a perspective view of the largest part of the outer surface of the inner part 3, while FIG. 3b contains a view of a part of the inner surface.

The inner part 3 is made of plastic material and has a basic element 17 having a plate-like design, starting from which a shaft 18 extends. Three passage holes 6, into which screws can be inserted for fastening the inner part to a medical device, in particular to a treatment lamp or an operating lamp, are provided as fastening means in the area of the plate-like basic element 17. Furthermore, a bracket 19 with a groove-shaped opposing element 7 for receiving the snap-in element 5 of the outer part 4 is provided on the plate-like basic element 17 in the area of the outer circumference 20. During the locking of the outer part 4 with the inner part 3, this opposing element 7 is meshed with the snap-in element 5 of the outer part 4 and these two elements 5, 7 are moved in relation to one another such that the snap-in element 5 is locked within the opposing element 7 with a wedge-shaped receptacle of the opposing element 7. To release the locking, the snap-in element 5 of the outer part 4 is moved in relation to the opposing element 7 of the inner part 3 such that the two elements 5, 7 are not meshed with one another any longer. A detachment of the locking, without having to have previously actively actuated the actuating element 8 for moving the snap-in element 5 in relation to the opposing element 7, is only possible with a comparatively great exertion of force, which cannot be manually applied during the usual operation. An undesired detachment of the outer part 4 from the inner part 3 is reliably avoided in this way.

Furthermore, three threaded teeth 21, which form an outer thread on the inner part 3, which can be meshed with an inner thread on the outer part 4 in case of correspondingly configured threaded teeth 22, are provided on the outer circumference of the plate-like basic element 14 such that the outer part 4 performs a screwing movement by means of a rotary motion in relation to the inner part 3 and the outer part 4 is consequently displaced in relation to the inner part 3 in the longitudinal direction of both parts. The inner part 3 thus has three short threaded teeth 21 on the circumference, with which threaded teeth 22 of the outer part 4 complementary hereto mesh at the same time as soon as the outer part 4 is mounted onto the inner part 3 and is rotated clockwise in relation to the inner part 3.

While the threaded teeth 21, 22 are meshed with each other, the snap-in element 5, which is arranged on the outer part 4 on the circumference, with its wedge-shaped snap-in contour 23, enters into the complementary opposing contour 24 of the opposing element 7 which is arranged on the inner part 3 and finally locks, and the locking takes place in a manner that is clearly audible to the operator. After the locking is completed, the rotary motion of the outer part 4 toward the inner part 3 is blocked in both directions. The elasticity of the material of the outer part 4 is utilized for the automatic locking by the wedge-shaped snap-in contour 23 being slid along a complementarily configured ramp of the opposing contour during the locking process, the snap-in element 5 is consequently moved in relation to the inner part 3 into a tensioned position and finally audibly snaps into the slightly pretensioned position upon reaching the locked position.

Figures 4A, 4B:
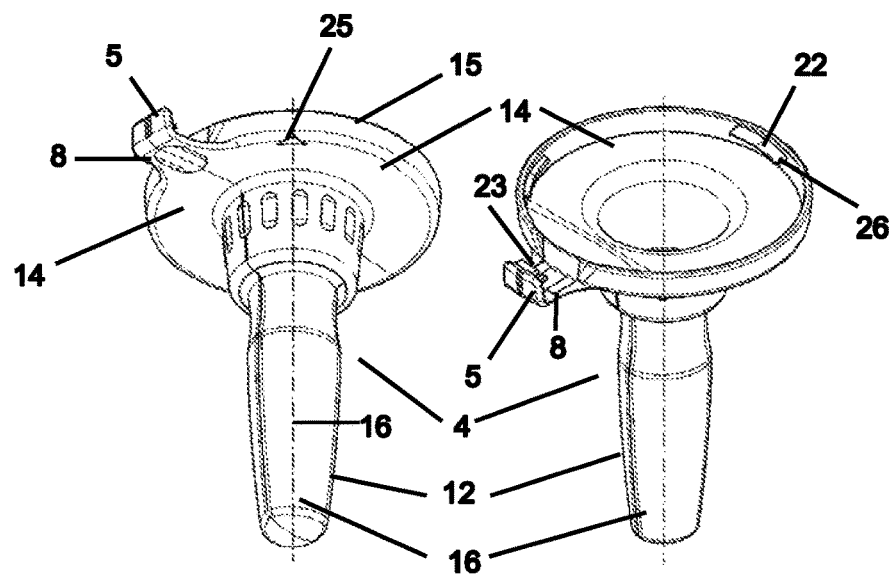
FIG. 4a is a lower perspective view of the outer part of the grip.
FIG. 4b is an upper perspective view of the outer part of the grip.

FIGS. 4a and 4b show, in two perspective views, an outer part 4 of a grip 1 configured according to the present invention for a medical device. In this connection, FIG. 4a shows the outer surface lying in the sterile area, especially the gripping surface, while FIG. 4b contains a view of the inner surface of the basic element 14, which also has a plate-like design, with the contact protection collar 15 and the threaded teeth 22 provided therein, which form an inner thread.

The outer part 4 is configured as essentially complementary to the inner part 3 and is also a component made of plastic material. The gripping surface 12 of the outer part 12 is shaped ergonomically such that a simple grasping of the grip 1 is possible and also a slipping off of the hand of the operator during a movement of the medical device 2 connected to the grip 1 is reliably avoided. Furthermore, on the outer circumference of the outer part 4 is provided an actuating element 8 in the form of a spring arm bracket, which has a snap-in element 5 with a snap-in contour 23, which is meshed with the complementary opposing contour 24 of the inner part 3 during the locking.

The actuating element 8 in the form of a bracket or a spring arm has an elastic design in this case such that the spring arm bracket is moved during the locking process and is finally locked into the locked position in an audible manner. In the locked position, the spring arm is tension-free or only slightly pretensioned. For automatic locking, the elasticity of the material of the outer part 4 is consequently used by the connection between the basic element 14 and the actuating element 8 with snap-in element 5 of the outer part being configured in the form of a spring arm. During the locking process, this spring arm has a slight pretension in relation to the locked position. As soon as the spring arm is in the locked state, it is only slightly pretensioned again. First for detaching the locking, the actuating element 8, which is configured as a spring arm, is again tensioned by pressing and consequently the snap-in contour 23 of the snap-in element 5 on the outer part is moved toward the opposing contour 24 of the opposing element 7 on the inner part 3 such that the a snap-in contour 23 of the snap-in element 23 can finally be removed from the complementary opposing contour 24 of the opposing element 7 by rotating the outer grip 4.

In the mounted position, the outer part 4 is supported, on the one hand, with the inner surface of the plate-like basic element 14 on the outer surface of the plate-like basic element 17 of the inner part 3. The threaded teeth 22 provided on the inside of the plate-like basic element 14 of the outer part mesh here with the complementary threaded teeth 21 on the outer surface of the plate-like basic element 17 of the inner part 3. The threaded teeth 21, 22 pull the plate surfaces toward one another in this case in an almost backlash-free manner. Further, the shaft 18 of the inner part 3 is supported at the lower end in the inner contour of the shaft 16 of the outer part 4.

The snap-in element 5, which is located on the actuating element 8, which is configured as a spring arm, has a thumb recess or finger recess on the surface of the actuating element 8 facing away from the snap-in contour 23 in order to make possible a preferred operation of the actuating element with the snap-in element 5. In this connection, it is possible for an operator to grasp the grip 1 with one hand and, for example, to press with his thumb on the bracket-like actuating element in order to thus detach the locking in a specific manner. In this case, the spring arm is tensioned again such that the snap-in contour 23 is detached from the complementary opposing contour 24 of the inner part 3 and the outer part 4 can finally be detached from the inner part 3 by means of a rotation in the counterclockwise direction. The unlocking and removal of the outer part 4 from the inner part 3 is thus also possible with one hand in a simple manner.

Figure 5B:
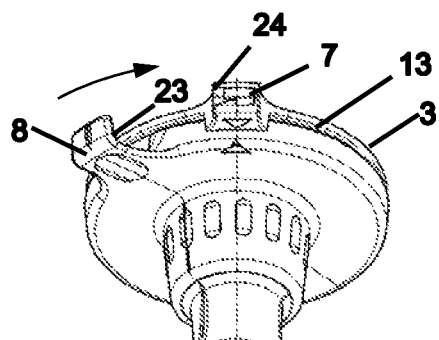
FIG. 5b is a perspective view showing the connection rotation of the outer part relative to the inner part of a grip.
Figure 5C:
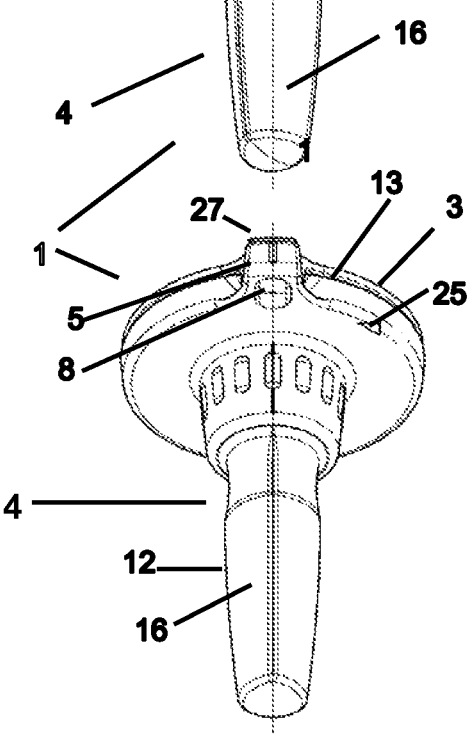
FIG. 5c is a perspective view showing the fastening and locking of the outer part to the inner part of a grip.

FIGS. 5*a*, 5*b* and 5*c* show the mounting, rotation and locking of the outer part 4 on the inner part 3 at different times of the locking process. FIG. 5*a* shows the grip at a time, in which the outer part and the inner part 4, 3 are still separated from one another.

Furthermore, the outer part 4 with outer shaft 17 is first mounted above the shaft 18 of the inner part 3 with movement of the outer part 4 in the direction of the arrow in FIG. 5*a*. In order to prevent the outer part 4 from being set at an incorrect angle, at which the threaded teeth 21, 22 would then be meshed with one another, but the snap-in mechanism would not grip, one of the threaded teeth on the inner part 3 as well as the threaded tooth on the outer part 4 that is complementary thereto is configured as being larger than the two remaining threaded teeth. It is consequently ensured that if the outer part 4 is set at an incorrect angle to the inner part 3 and is then rotated clockwise, the threaded teeth 21, 22 do not mesh, since the enlarged threaded tooth (of the outer part 4) slides on the plate-shaped outer surface of the inner part 3. In case of further rotation in the clockwise direction, the outer part strikes against one of the threaded teeth 21 of the inner part with a boss 26 molded in one piece with one of the threaded teeth 22 such that the rotation is blocked without the grip locking. Only if the outer part is set in an angle range, in which the two enlarged threaded teeth approach each other, the outer part 4 can move closer to the inner part 3 by the enlarged threaded tooth sliding along on a slope of the inner part 3 such that the threaded teeth can mesh with one another upon further rotation of the outer part 4.

In order to help the user, moreover, to find the correct position from the outer part to the inner part 4, 3, a mark 25, which indicates to the operator how he has to place the outer part 4 onto the inner part 3 in order to reach, starting from there, the locked position by rotating clockwise using the shortest path possible, is provided at least either on the outer part or on the inner part 4, 3, and preferably on both parts.

During the rotary motion of the outer part 4 in relation to the inner part 3, as can be seen in FIG. 5*b*, the threaded teeth 22 of the outer part 4 come into contact with the threaded teeth 21 of the inner part 3, and the snap-in contour 23 provided on the circumference of the outer part 4 meshes with the complementary opposing contour 24 on the inner part 3. The clockwise rotary motion is continued until, as shown in FIG. 5*c*, the snap-in contour 5 locks in an audible manner in the opposing contour 24 of the inner part 3. The rotary motion is blocked in both directions after the locking process has been carried out. The elasticity of the material of the outer part 4 is used for automatic locking, and the connection between the basic element 14 of the outer part 4 and the actuating element 8 with snap-in element 5, which has a snap-in contour 23, is configured in the form of a spring arm. This spring arm has a pretension against the locked position during the locking process.

Figure 6A:
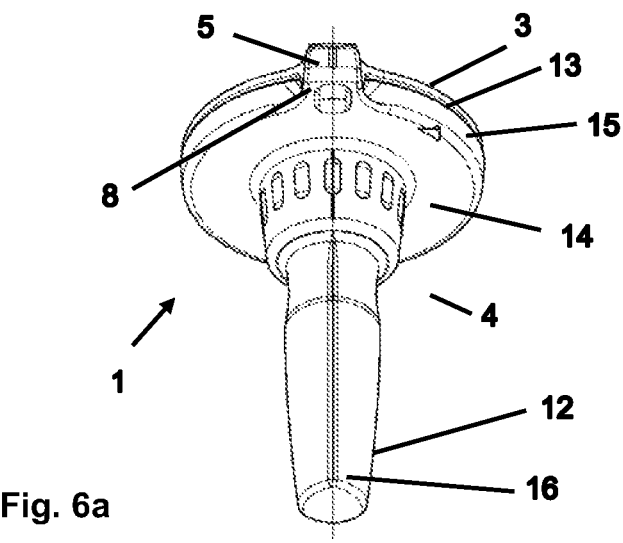
FIG. 6a is a perspective view showing the unlocking of the outer part from the inner part of a grip.
Figure 6B:
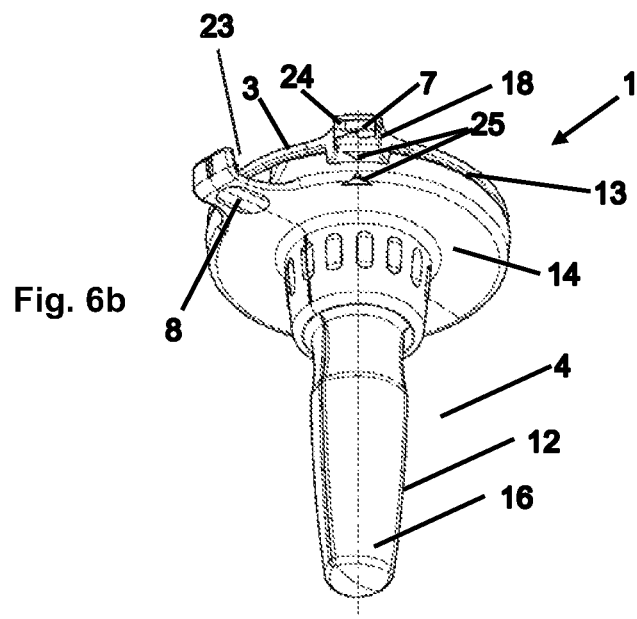
FIG. 6b is a perspective view showing the disconnection rotation of the outer part relative to the inner part of a grip.

FIGS. 6*a*, 6*b* and 6*c* show the unlocking process. FIG. 6*a* shows the handle 1 first in a state, in which the outer part 4 is locked with the inner part 3, the snap-in contour 23 of the outer part 4 thus meshing with low backlash with the complementary opposing contour 24 of the opposing element 7 on the inner part.

By pressing the actuating element 8, with a thumb recess on the top side, which is configured as a spring arm, the snap-in element 5 is moved and unlocks the snap-in contour 23 thereof against the opposing contour 24. At the same time, the outer part 4 is rotated counterclockwise, as can be seen in FIG. 6*b*. This rotation is continued until the threaded teeth 21, 22 of the outer part and of the inner part 4, 3 are no longer meshed such that the outer part 4 can be removed from the inner part 3 with movement of the outer part 4 in the direction of the arrow in FIG. 6*c*. The outer part 4 and the inner part 3 are, as is shown in FIG. 6*c*, again in a state separated from one another such that the outer part 4 can now be fed to a sterilization process as needed.

The technical solution according to the present invention, which essentially comprises a grip for a medical device, which has an outer part and an inner part, which can be locked with one another, and the outer part has a one-piece design, is characterized in that, on the one hand, the outer part can be mounted onto the inner part and can be removed from the inner part in a particularly simple manner, and, on the other hand, in that the outer part, because of its design, can be cleaned, disinfected and/or sterilized in a reliable manner.

The outer part and the inner part 4, 3 thus preferably consist of only one plastic part each, which has both advantages in terms of the necessary hygiene and the costs in the manufacture of the grip 1. The locking shown is, furthermore, easy to actuate, and the locking can be perceived by the operator by a clearly audible sound, in particular, a clicking. A certain transmission of force from the outer part 4 to the inner part 3 is guaranteed in the locked state. In relation to possible transverse motions during the actuation of the grip 1, a certain support is provided via the threaded teeth 21, 22, the plate surfaces 14, 17 and the shafts 16, 18 of the outer part and of the inner part 4, 3.

In the direction of rotation of the grip 1, the locking mechanism 27 functions at a great lever distance to the grip axis. In addition, the elasticity of the actuating element 8, which is preferably configured as a spring arm, brings about, by means of torsion deformation, that the snap-in element 5 with its snap-in contour 23 is set so oblique in case of counterclockwise torque stress that an automatic unlocking is counteracted. Further, the outer part 4 and the actuating element 8 are configured such that the outer part 4 at least almost entirely overlaps the inner part 3 such that an inadvertent contact with the inner part 3 or with other areas, for example, with an operating lamp, is unlikely.

The unlocking takes place with little force, preferably by means of thumb pressure on a recess on the actuating element 8 provided for this and effortless counterclockwise rotation by a small angle. In this case, only the outer part 4 is contacted. The preferred actuating element 8 is preferably removed so far from the actual gripping surface 12 that inadvertent unlocking is reliably avoided or is unlikely. Besides the ergonomics of the outer part 4, the inner part 3 has a correspondingly ergonomic shape as well such that it can also be used for positioning the medical device. For example, the operating staff can preposition the operating lamp on this unsterile inner part and then put on the usually sterile outer part.

While specific embodiments of the invention have been shown and described in detail to illustrate the application of the principles of the invention, it will be understood that the invention may be embodied otherwise without departing from such principles.

APPENDIX

List of Reference Numbers

1 Grip
2 Medical device
3 Inner part
4 Outer part
5 Snap-in element on the outer part
6 Fastening means
7 Opposing element on the inner part
8 Actuating element
9 Light fixture housing
10 Light source
11 Light emission area
12 Gripping surface
13 Gap
14 Basic element of the outer part
15 Contact protection collar
16 Shaft of the outer part
17 Basic element of the inner part
18 Shaft of the inner part
19 Bracket on the inner part
20 Outer circumference of the inner part
21 Threaded tooth on the inner part
22 Threaded tooth on the outer part
23 Snap-in contour of the snap-in element
24 Opposing contour of the opposing
25 Mark
26 Stop boss
27 Locking mechanism

What is claimed is:

1. A medical device grip comprising:
an inner part comprising: a fastening means for fastening the inner part to a medical device; and a snap opposing element; and
an outer part comprising: a snap-in element engageable in a locking manner with the snap opposing element of the inner part for a detachable fastening of the outer part to the inner part, wherein in a fastened locked state, the outer part at least partially overlaps surfaces facing away from a connected medical device; and an actuating element provided on the outer part, the actuating element being manually actuatable for unlocking the snap-in element for detachment of the outer part, wherein the actuating element has a one-piece configuration with the snap-in element and the outer part such that the actuating element performs a movement with the snap-in element in relation to the snap opposing element during the unlocking, the inner part having at least one threaded tooth on an inner part outer surface, wherein a complementary threaded tooth is arranged on an outer part inside, the at least one threaded tooth being engageable with the complementary threaded tooth.

2. A medical device grip in accordance with claim 1, wherein the inner part and the outer part comprise at least one plastic on outer surfaces thereof.

3. A medical device grip in accordance with claim 1, wherein, in the locked state, a force can be transmitted from the outer part to the inner part via the snap-in element and the snap opposing element.

4. A medical device grip in accordance with claim 1, wherein the at least one threaded tooth and the complementary threaded tooth are configured as a right-hand thread.

5. A medical device grip in accordance with claim 1, wherein the at least one threaded tooth and the complementary threaded tooth are arranged and configured such that the outer part and the inner part can be brought to a minimal distance spacing relative to one another upon joining the at least one threaded tooth and the complementary threaded tooth and rotating the outer part relative to the inner part in a predetermined angle range.

6. A medical device grip in accordance with claim 1, wherein the snap-in element is connected in a spring-loaded manner to the outer part.

7. A medical device grip in accordance with claim 1, wherein the actuating element has a spring arm.

8. A medical device grip in accordance with claim 7, wherein the actuating element has a gripping surface.

9. A medical device grip in accordance with claim 1, wherein the outer part at least almost entirely overlaps the inner part in the locked state.

10. A medical device grip in accordance with claim 1, wherein the at least one threaded tooth and the complementary threaded tooth are arranged and configured such that the inner part and the outer part can be joined such that a locking using a shortest path is possible.

11. A medical device grip in accordance with claim 1, in combination with an examination lamp or in combination with an operating lamp.

12. A medical device grip in accordance with claim 1, wherein the outer part is made in one piece to define a contiguous closed outer surface which has no gaps.

13. A medical device grip comprising:
an inner part comprising: a fastening means for fastening the inner part to a medical device; and a snap opposing element; and
an outer part comprising: a snap-in element engageable in a locking manner with the snap opposing element of the inner part for a detachable fastening of the outer part to the inner part, wherein in a fastened locked state, the outer part at least partially overlaps surfaces facing away from a connected medical device; and an actuating element provided on the outer part, the actuating element comprising a spring arm, the snap-in element being arranged on the spring arm, the actuating element being manually actuateable for unlocking the snap-in element for detachment of the outer part, wherein the actuating element has a one-piece configuration with the snap-in element and the outer part such that the actuating element performs a movement with the snap-in element in relation to the snap opposing element during the unlocking, the inner part having at least one threaded tooth on an inner part outer surface, wherein a complementary threaded tooth is arranged on an outer part inside, the at least one threaded tooth is engageable with the complementary threaded tooth.

14. A medical device grip in accordance with claim 13, wherein the at least one threaded tooth and the complementary threaded tooth are configured as a right-hand thread.

15. A medical device grip in accordance with claim 13, wherein the at least one threaded tooth and the complementary threaded tooth are arranged and configured such that the outer part and the inner part can be brought to a minimal distance spacing relative to one another upon joining the at least one threaded tooth and the complementary threaded tooth and rotating the outer part relative to the inner part in a predetermined angle range.

16. A medical device grip in accordance with claim 13, wherein the at least one threaded tooth and the complementary threaded tooth are arranged and configured such that the inner part and the outer part can be joined such that a locking using a shortest path is possible.

17. A medical device grip, comprising:
an inner part comprising: a fastening means for fastening the inner part to a medical device; and a snap opposing element; and
an outer part comprising: a snap-in element engageable in a locking manner with the snap opposing element of the inner part for a detachable fastening of the outer part to the inner part, wherein in a fastened locked state, the outer part at least partially overlaps surfaces facing away from a connected medical device; and an actuating element provided on the outer part, the actuating element comprising a spring arm, the snap-in element being arranged on the spring arm, the actuating element being manually actuatable for unlocking the snap-in element for detachment of the outer part, wherein the actuating element has a one-piece configuration with the snap-in element and the outer part such that the actuating element performs a movement with the snap-in element in relation to the snap opposing element during the unlocking, wherein the spring arm extends in a radial direction with respect to a longitudinal axis of the outer part, wherein at least a portion of the snap-in element is located at an axially spaced location from the spring arm with respect to the longitudinal axis.

18. A medical device grip in accordance with claim 17, wherein the outer part comprises a collar, the collar comprising an outer surface, the collar enclosing at least a portion of the inner part when the outer part is detachably fastened to the inner part, the spring arm extending to a position located radially beyond the outer surface, wherein the snap-in element is located at a radially spaced location from the outer surface.

19. A medical device grip, comprising:
an inner part comprising: a fastening means for fastening the inner part to a medical device; and a snap opposing element; and
an outer part comprising: a snap-in element engageable in a locking manner with the snap opposing element of the inner part for a detachable fastening of the outer part to the inner part, wherein in a fastened locked state, the outer part at least partially overlaps surfaces facing away from a connected medical device; and an actuating element provided on the outer part, the actuating element being manually actuatable for unlocking the snap-in element for detachment of the outer part, wherein the actuating element has a one-piece configuration with the snap-in element and the outer part such that the actuating element performs a movement with the snap-in element in relation to the snap opposing element during the unlocking, the inner part having at least one threaded tooth on an inner part outer surface, wherein a complementary threaded tooth is arranged on an outer part inside, the at least one threaded tooth being engageable with the complementary threaded tooth, wherein the outer part comprises a plate-shaped basic element, the plate-shaped basic element enclosing at least a portion of the inner part when the outer part is detachably fastened to the inner part, the spring arm extending in a radial direction from the plate-shaped basic element with respect to a longitudinal axis of the outer part, wherein the spring arm defines a radial extension of the plate-shaped basic element.

* * * * *